(12) United States Patent
Demond et al.

(10) Patent No.: US 7,625,389 B2
(45) Date of Patent: Dec. 1, 2009

(54) EMBOLIC PROTECTION DEVICE

(75) Inventors: Jackson Demond, Santa Cruz, CA (US);
Jeff Krolik, Campbell, CA (US);
Richard J. Renati, Los Gatos, CA (US);
Amr Salahieh, Saratoga, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 884 days.

(21) Appl. No.: 10/331,380

(22) Filed: Dec. 30, 2002

(65) Prior Publication Data

US 2004/0127933 A1    Jul. 1, 2004

(51) Int. Cl.
*A61M 29/00* (2006.01)
(52) U.S. Cl. .................................... 606/200
(58) Field of Classification Search ............. 606/159, 606/200
See application file for complete search history.

(56) References Cited

U.S. PATENT DOCUMENTS

| | | | |
|---|---|---|---|
| 3,472,230 A | 10/1969 | Fogarty | |
| 3,952,747 A | 4/1976 | Kimmell, Jr. | |
| 3,996,938 A | 12/1976 | Clark, III | |
| 4,046,150 A | 9/1977 | Schwartz et al. | |
| 4,425,908 A | 1/1984 | Simon | |
| 4,590,938 A | 5/1986 | Segura et al. | |
| 4,619,246 A | 10/1986 | Molgaard-Nielsen et al. | |
| 4,650,466 A | 3/1987 | Luther | |
| 4,706,671 A | 11/1987 | Weinrib | |
| 4,723,549 A | 2/1988 | Wholey et al. | |
| 4,790,812 A | 12/1988 | Hawkins, Jr. et al. | |
| 4,790,813 A | 12/1988 | Kensey | |
| 4,794,928 A | 1/1989 | Kletschka | |
| 4,807,626 A | 2/1989 | McGirr | |
| 4,842,579 A | 6/1989 | Shiber | |
| 4,873,978 A | 10/1989 | Ginsburg | |
| 4,921,478 A | 5/1990 | Solano et al. | |
| 4,921,484 A | 5/1990 | Hillstead | |
| 4,926,858 A | 5/1990 | Gifford, III et al. | |
| 4,969,891 A | 11/1990 | Gewertz | |
| 4,998,539 A | 3/1991 | Delsanti | |
| 5,002,560 A | 3/1991 | Machold et al. | |
| 5,011,488 A | 4/1991 | Ginsburg | |
| 5,053,008 A | 10/1991 | Bajaj | |
| 5,071,407 A | 12/1991 | Termin et al. | |

(Continued)

FOREIGN PATENT DOCUMENTS

DE    28 21 048    7/1980

(Continued)

OTHER PUBLICATIONS

"Atherosclerotic Disease of the Aortic Arch as a Risk Factor of Recurrent Ischemic Stroke," *The New England Journal of Medicine*, pp. 1216-1221 (May 1996).

(Continued)

*Primary Examiner*—Anhtuan T Nguyen
*Assistant Examiner*—Tuan V Nguyen
(74) *Attorney, Agent, or Firm*—Crompton, Seager & Tufte LLC

(57) ABSTRACT

An embolic protection filter. In some embodiments, the device includes an elongate shaft, a filter coupled to the shaft, and a proximal stop coupled to the shaft.

2 Claims, 2 Drawing Sheets

U.S. PATENT DOCUMENTS

| | | | |
|---|---|---|---|
| 5,100,423 A | 3/1992 | Fearnot | |
| 5,102,415 A | 4/1992 | Guenther et al. | |
| 5,133,733 A | 7/1992 | Rasmussen et al. | |
| 5,152,771 A | 10/1992 | Sabbaghian et al. | |
| 5,152,777 A | 10/1992 | Goldberg et al. | |
| 5,160,342 A | 11/1992 | Reger et al. | |
| 5,224,945 A | 7/1993 | Pannek, Jr. | |
| 5,224,953 A | 7/1993 | Morgentaler | |
| 5,226,909 A | 7/1993 | Evans et al. | |
| 5,312,427 A | 5/1994 | Shturman | |
| 5,314,438 A | 5/1994 | Shturman | |
| 5,329,942 A | 7/1994 | Gunther et al. | |
| 5,330,484 A | 7/1994 | Gunther | |
| 5,354,310 A | 10/1994 | Garnie et al. | |
| 5,356,418 A | 10/1994 | Shturman | |
| 5,376,100 A | 12/1994 | Lefebvre | |
| 5,421,832 A | 6/1995 | Lefebvre | |
| 5,423,742 A | 6/1995 | Theron | |
| 5,443,443 A | 8/1995 | Shiber | |
| 5,449,372 A | 9/1995 | Schmaltz et al. | |
| 5,456,667 A | 10/1995 | Ham et al. | |
| 5,462,529 A | 10/1995 | Simpson et al. | |
| 5,536,242 A | 7/1996 | Willard et al. | |
| 5,549,626 A | 8/1996 | Miller et al. | |
| 5,601,595 A * | 2/1997 | Smith | 606/200 |
| 5,622,188 A | 4/1997 | Plaia et al. | |
| 5,632,755 A | 5/1997 | Nordgren et al. | |
| 5,658,296 A | 8/1997 | Bates et al. | |
| 5,662,671 A | 9/1997 | Barbut et al. | |
| 5,695,519 A | 12/1997 | Summers et al. | |
| 5,720,764 A | 2/1998 | Naderlinger | |
| 5,728,066 A | 3/1998 | Daneshvar | |
| 5,749,848 A | 5/1998 | Jang et al. | |
| 5,769,816 A | 6/1998 | Barbut et al. | |
| 5,779,716 A | 7/1998 | Cano et al. | |
| 5,792,157 A | 8/1998 | Mische et al. | |
| 5,795,322 A | 8/1998 | Boudewijn | |
| 5,800,457 A | 9/1998 | Gelbfish | |
| 5,800,525 A | 9/1998 | Bachinski et al. | |
| 5,810,874 A | 9/1998 | Lefebvre | |
| 5,814,064 A | 9/1998 | Daniel et al. | |
| 5,827,324 A | 10/1998 | Cassell et al. | |
| 5,833,644 A | 11/1998 | Zadno-Azizi et al. | |
| 5,833,650 A | 11/1998 | Imran | |
| 5,836,868 A | 11/1998 | Ressemann et al. | |
| 5,846,260 A | 12/1998 | Maahs | |
| 5,848,964 A | 12/1998 | Samuels | |
| 5,876,367 A | 3/1999 | Kaganov et al. | |
| 5,882,329 A | 3/1999 | Patterson et al. | |
| 5,895,399 A | 4/1999 | Barbut et al. | |
| 5,897,567 A | 4/1999 | Ressemann et al. | |
| 5,910,154 A | 6/1999 | Tsugita et al. | |
| 5,911,734 A | 6/1999 | Tsugita et al. | |
| 5,925,016 A | 7/1999 | Chornenky et al. | |
| 5,925,060 A | 7/1999 | Forber | |
| 5,925,062 A | 7/1999 | Purdy | |
| 5,935,139 A | 8/1999 | Bates | |
| 5,941,869 A | 8/1999 | Patterson et al. | |
| 5,941,896 A | 8/1999 | Kerr | |
| 5,947,995 A | 9/1999 | Samuels | |
| 5,954,745 A | 9/1999 | Gertler et al. | |
| 5,980,555 A | 11/1999 | Barbut et al. | |
| 5,989,281 A | 11/1999 | Barbut et al. | |
| 5,993,469 A | 11/1999 | McKenzie et al. | |
| 5,997,557 A | 12/1999 | Barbut et al. | |
| 6,001,118 A | 12/1999 | Daniel et al. | |
| 6,007,557 A | 12/1999 | Ambrisco et al. | |
| 6,010,522 A | 1/2000 | Barbut et al. | |
| 6,013,085 A | 1/2000 | Howard | |
| 6,027,520 A | 2/2000 | Tsugita et al. | |
| 6,042,598 A | 3/2000 | Tsugita et al. | |
| 6,051,014 A | 4/2000 | Jang | |
| 6,051,015 A | 4/2000 | Maahs | |
| 6,053,932 A | 4/2000 | Daniel et al. | |
| 6,059,814 A | 5/2000 | Ladd | |
| 6,066,149 A | 5/2000 | Samson et al. | |
| 6,066,158 A | 5/2000 | Engelson et al. | |
| 6,068,645 A | 5/2000 | Tu | |
| 6,086,605 A | 7/2000 | Barbut et al. | |
| 6,099,546 A * | 8/2000 | Gia | 606/191 |
| 6,102,932 A * | 8/2000 | Kurz | 606/200 |
| 6,117,154 A | 9/2000 | Barbut et al. | |
| 6,129,739 A * | 10/2000 | Khosravi | 606/200 |
| 6,136,016 A | 10/2000 | Barbut et al. | |
| 6,142,987 A | 11/2000 | Tsugita | |
| 6,152,946 A | 11/2000 | Broome et al. | |
| 6,156,046 A | 12/2000 | Passafaro et al. | |
| 6,165,200 A | 12/2000 | Tsugita et al. | |
| 6,168,579 B1 | 1/2001 | Tsugita | |
| 6,171,327 B1 * | 1/2001 | Daniel et al. | 606/200 |
| 6,171,328 B1 | 1/2001 | Addis | |
| 6,179,851 B1 | 1/2001 | Barbut et al. | |
| 6,179,859 B1 | 1/2001 | Bates et al. | |
| 6,179,861 B1 | 1/2001 | Khosravi et al. | |
| 6,203,561 B1 | 3/2001 | Ramee et al. | |
| 6,206,868 B1 | 3/2001 | Parodi | |
| 6,214,026 B1 | 4/2001 | Lepak et al. | |
| 6,221,006 B1 | 4/2001 | Dubrul et al. | |
| 6,224,620 B1 | 5/2001 | Maahs | |
| 6,231,544 B1 | 5/2001 | Tsugita et al. | |
| 6,235,044 B1 | 5/2001 | Root et al. | |
| 6,235,045 B1 | 5/2001 | Barbut et al. | |
| 6,238,390 B1 * | 5/2001 | Tu et al. | 606/41 |
| 6,238,412 B1 | 5/2001 | Dubrul et al. | |
| 6,245,012 B1 | 6/2001 | Kleshinski | |
| 6,245,087 B1 | 6/2001 | Addis | |
| 6,245,088 B1 | 6/2001 | Lowery | |
| 6,245,089 B1 | 6/2001 | Daniel et al. | |
| 6,258,115 B1 | 7/2001 | Dubrul | |
| 6,264,663 B1 | 7/2001 | Cano | |
| 6,264,672 B1 | 7/2001 | Fisher | |
| 6,270,477 B1 * | 8/2001 | Bagaoisan et al. | 604/96.01 |
| 6,270,513 B1 | 8/2001 | Tsugita et al. | |
| 6,277,138 B1 | 8/2001 | Levinson et al. | |
| 6,277,139 B1 * | 8/2001 | Levinson et al. | 606/200 |
| 6,280,413 B1 | 8/2001 | Clark et al. | |
| 6,287,321 B1 | 9/2001 | Jang | |
| 6,290,710 B1 | 9/2001 | Cryer et al. | |
| 6,309,399 B1 | 10/2001 | Barbut et al. | |
| 6,319,268 B1 | 11/2001 | Ambrisco et al. | |
| 6,336,934 B1 | 1/2002 | Gilson et al. | |
| 6,344,049 B1 | 2/2002 | Levinson et al. | |
| 6,371,971 B1 | 4/2002 | Tsugita et al. | |
| 6,383,206 B1 | 5/2002 | Gillick et al. | |
| 6,432,122 B1 * | 8/2002 | Gilson et al. | 606/200 |
| 6,443,926 B1 | 9/2002 | Kletschka | |
| 6,468,291 B2 * | 10/2002 | Bates et al. | 606/200 |
| 6,551,341 B2 * | 4/2003 | Boylan et al. | 606/200 |
| 6,656,202 B2 * | 12/2003 | Papp et al. | 606/200 |
| 6,818,006 B2 * | 11/2004 | Douk et al. | 606/200 |
| 2002/0055747 A1 | 5/2002 | Cano et al. | |
| 2002/0095170 A1 | 7/2002 | Krolik et al. | |
| 2002/0128679 A1 | 9/2002 | Turovskiy et al. | |
| 2002/0161390 A1 * | 10/2002 | Mouw | 606/200 |

FOREIGN PATENT DOCUMENTS

| | | |
|---|---|---|
| DE | 34 17 738 | 11/1985 |
| DE | 40 30 998 A1 | 10/1990 |
| DE | 199 16 162 | 10/2000 |
| EP | 0 200 688 | 11/1986 |
| EP | 0 293 605 A1 | 12/1988 |
| EP | 0 411 118 A1 | 2/1991 |
| EP | 0 427 429 A2 | 5/1991 |

| | | |
|---|---|---|
| EP | 0 437 121 B1 | 7/1991 |
| EP | 0 472 334 A1 | 2/1992 |
| EP | 0 472 368 A2 | 2/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 0 934 729 | 8/1999 |
| EP | 1 127 556 A2 | 8/2001 |
| FR | 2 580 504 | 10/1986 |
| FR | 2 643 250 A1 | 8/1990 |
| FR | 2 666 980 | 3/1992 |
| FR | 2 694 687 | 8/1992 |
| FR | 2 768 326 A1 | 3/1999 |
| GB | 2 020 557 B | 1/1983 |
| JP | 8-187294 A | 7/1996 |
| SU | 764684 | 9/1980 |
| WO | WO 88/09683 | 12/1988 |
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/10375 | 4/1996 |
| WO | WO 96/19941 | 7/1996 |
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07521 | 2/2000 |
| WO | WO 00/07655 | 2/2000 |
| WO | WO 00/09054 | 2/2000 |
| WO | WO 00/16705 | 3/2000 |
| WO | WO 00/49970 | 8/2000 |
| WO | WO 00/53120 | 9/2000 |
| WO | WO 00/67664 | 11/2000 |
| WO | WO 00/67665 | 11/2000 |
| WO | WO 00/67666 | 11/2000 |
| WO | WO 00/67668 | 11/2000 |
| WO | WO 00/67669 | 11/2000 |
| WO | WO 01/05462 | 1/2001 |
| WO | WO 01/08595 | 2/2001 |
| WO | WO 01/08596 | 2/2001 |
| WO | WO 01/08742 | 2/2001 |
| WO | WO 01/08743 | 2/2001 |
| WO | WO 01/10320 | 2/2001 |
| WO | WO 01/15629 | 3/2001 |
| WO | WO 01/21077 | 3/2001 |
| WO | WO 01/21100 | 3/2001 |
| WO | WO 01/26726 | 4/2001 |
| WO | WO 01/35857 | 5/2001 |
| WO | WO 01/43662 | 6/2001 |
| WO | WO 01/47579 | 7/2001 |
| WO | WO 01/49208 | 7/2001 |
| WO | WO 01/49209 | 7/2001 |
| WO | WO 01/49215 | 7/2001 |
| WO | WO 01/49355 | 7/2001 |
| WO | WO 01/52768 | 7/2001 |
| WO | WO 01/58382 | 8/2001 |
| WO | WO 01/60442 | 8/2001 |
| WO | WO 01//67989 | 9/2001 |
| WO | WO 01/70326 | 9/2001 |
| WO | WO 01/72205 | 10/2001 |
| WO | WO 01/87183 | 11/2001 |
| WO | WO 01/89413 | 11/2001 |
| WO | WO 01/91824 | 12/2001 |
| WO | WO 01/11627 A2 | 2/2002 |
| WO | WO 02/060519 A1 | 8/2002 |
| WO | WO 02/094111 A2 | 11/2002 |

OTHER PUBLICATIONS

"Endovascular Grafts, Stents Drive Interventional Radiology Growth," *Cardiovascular Device Update*, 2(3):1-12 (Mar. 1996).

"Protruding Atheromas in the Thoracic Aortic and Systemic Embolization," pp. 423-427 American College of Physicians (1991).

"Recognition and Embolic Potential of Intraaortic Atherosclerotic Debris," American College of Cardiology (Jan. 1991).

Cragg, Andrew et al., "A New Percutaneous Vena Cava Filger," *AJR*, 141:601-604 (Sep. 1983).

Cragg, Andrew et al., "Nonsurgical Placement of Arterial Endoprosthesis: A New Technique Using Nitinol Wire," *AJR*, pp. 261-263 (Apr. 1983).

Diethrich et al., "Percutaneous Techniques for Endoluminal Carotid Interventions," *J. Endovasc. Surg.*, 3:182-202 (1996).

Fadali, A. Moneim, "A filtering device for the prevention of particulate embolization during the course of cardiac surgery," *Surgery*, 64(3):634-639 (Sep. 1968).

Haissaguerre et al., "Spontaneous Initiation of Atrial Fibrillation by Ectopic Beats Originating in the Pulmonary Veins," *The New England Journal of Medicine*, 339(10):659-666 (Sep. 1988).

Jordan, Jr. et al., "Microemboli Detected by Transcranial Doppler Monitoring . . . ," *Cardiovascular Surgery*, 7(1)33-38 (Jan. 1999).

Lesh, "Can Catheter Ablation Cure Atrial Fibrillation?" *ACC Current Journal Review*, pp. 38-40 (Sep./Oct. 1997).

Lund et al., "Long-Term Patentcy of Ductus Arteriosus After Balloon Dilation: an Experimental Study," *Laboratory Investigation*, 69(4):772-774 (Apr. 1984).

Marache et al., "Percutaneous Transluminal Venous Angioplasty . . . ," *American Heart Journal*, 125(2 Pt 1):362-366 (Feb. 1993).

Mazur et al., "Directional Atherectomy with the Omnicath™ : A Unique New Catheter System," *Catheterization and Cardiovascular Diagnosis*, 31:17-84 (1994).

Moussa, MD, Issaam "Stents Don't Require Systemic Anticoagulation . . . But the Technique (and Results) Must be Optimal," *Journal of Invasive Cardiol.*, 8(E):3E-7E, (1996).

Nakanishi et al., "Catheter Intervention to Venous System Using Expandable Metallic Stents," *Rinsho Kyobu Geka*, 14(2):English Abstract Only (Apr. 1994).

Onal et al., "Primary Stenting for Complex Atherosclerotic Plaques in Aortic and Iliac Stenoses," *Cardiovascular & Interventional Radiology*, 21(5):386-392 (1998).

Theron et al., "New Triple Coaxial Catheter System for Carotid Angioplasty with Cerebral Protection," *American Journal of Neuroradiology*, 11:869-874 (1990).

Tunick et al., "Protruding atherosclerotic plaque in the aortic archo f patients with systemic embolization: A new finding seen by transesophageal echocardiography," *American Heart Journal* 120(3):658-660 (Sep. 1990).

Waksman et al., "Distal Embolization is Common After Directional Atherectomy...," *American Heart Journal*, 129(3):430-435 (1995).

Wholey, Mark H. et al., PTA and Stents in the Treatment of Extracranial Circulation, *The Journal of Invasive Cardiology*, 8(E):25E-30E (1996).

* cited by examiner

EMBOLIC PROTECTION DEVICE

FIELD OF THE INVENTION

The present invention pertains to intravascular filtering devices. More particularly, the present invention pertains to devices for filtering embolic debris generated during intravascular medical interventions.

BACKGROUND

Heart and vascular disease are majors problem in the United States and throughout the world. Conditions such as atherosclerosis result in blood vessels becoming blocked or narrowed. This blockage can result in lack of oxygenation of the heart, which has significant consequences since the heart muscle must be well oxygenated in order to maintain its blood pumping action.

Occluded, stenotic, or narrowed blood vessels may be treated with a number of relatively non-invasive medical procedures including percutaneous transluminal angioplasty (PTA), percutaneous transluminal coronary angioplasty (PTCA), and atherectomy. Angioplasty techniques typically involve the use of a balloon catheter. The balloon catheter is advanced over a guidewire such that the balloon is positioned adjacent a stenotic lesion. The balloon is then inflated and the restriction of the vessel is opened. During an atherectomy procedure, the stenotic lesion may be mechanically cut away from the blood vessel wall using an atherectomy catheter.

During angioplasty and atherectomy procedures, embolic debris can be separated from the wall of the blood vessel. During angioplasty procedures, stenotic debris may also break loose due to manipulation of the blood vessel. Because of this debris, a number of devices, termed embolic protection devices, have been developed to filter out this debris.

Embolic debris can also be generated when performing an intravascular procedure at a location away from the heart. For example, engaging or treating the renal artery may generate embolic debris.

BRIEF SUMMARY OF THE INVENTION

The present invention incorporates design and manufacturing refinements to embolic protection devices. In some embodiments, a filter can be coupled to an elongate shaft. The shaft may comprise, for example, a guidewire. A proximal stop may be coupled to the shaft. The stop may be adapted and configured to essentially prevent a catheter from passing over the shaft distally beyond the stop and over the filter. The stop may also be configured to release therapeutic drugs or other appropriate substances.

DETAILED DESCRIPTION

Figure 1:
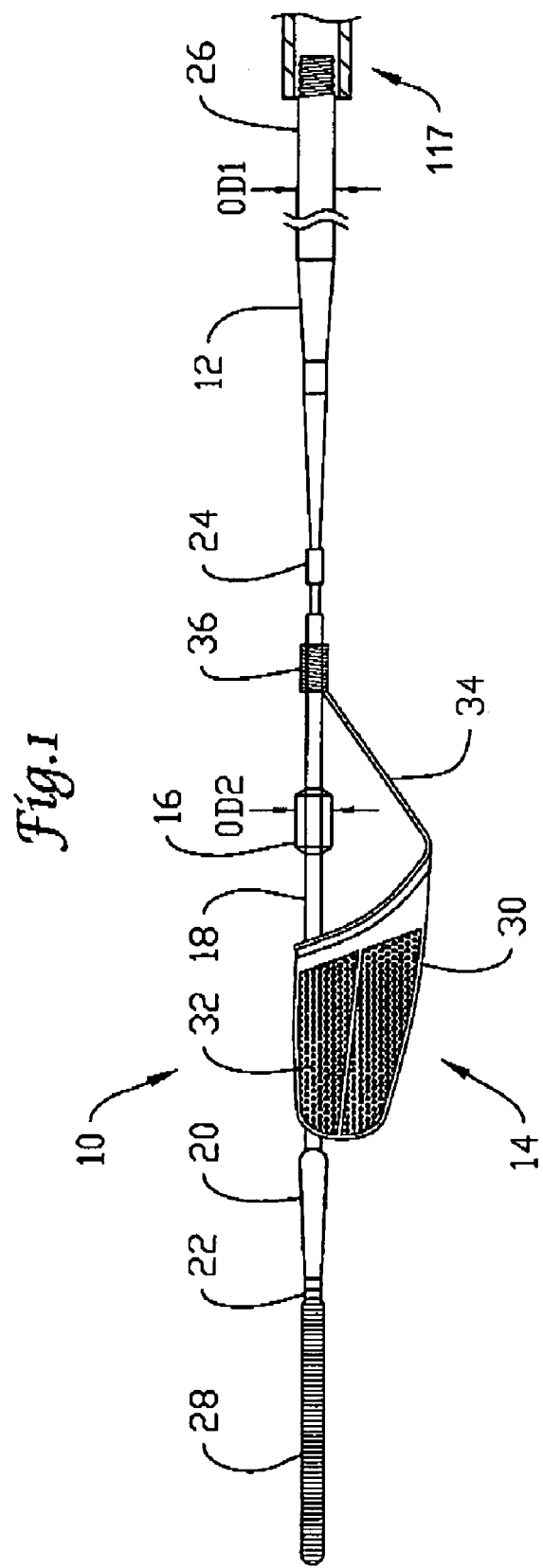
FIG. 1 is a side view of an embodiment of an embolic protection filtering device.

The following description should be read with reference to the drawings wherein like reference numerals indicate like elements throughout the several views. The detailed description and drawings illustrate example embodiments of the claimed invention.

Intravascular medical procedures such as angioplasty or atherectomy can generate embolic debris. This debris can travel in the bloodstream and possibly obstruct downstream vascular regions. FIG. 1 is a side view of an embodiment of an embolic protection filtering device 10 that may be used to filter out embolic debris. Device 10 includes an elongate shaft 12 having a filter 14 coupled thereto. A proximal stop 16 is coupled to shaft 12. Stop 16 is adapted and configured to stop a medical device such as a therapeutic catheter 117 from being advanced over shaft 14 beyond stop 16. Stop 16, thus, can prevent the medical device from being advanced distally over filer 14. A therapeutic catheter might be, for example, an angioplasty catheter, stent deployment catheter, atherectomy catheter or other device.

The majority of the length of shaft 12 can generally have a constant outside diameter, shown in FIG. 1 as OD1. OD1 is sized to allow other medical devices to pass over shaft 12 as needed for any given intervention. For example, an angioplasty or other catheter may be passed over shaft 12 in order to perform a medical procedure. According to this embodiment, shaft 12 can pass through a lumen disposed within the catheter. It can be appreciated that the size of OD1 can be varied for different medical devices without departing from the spirit of the invention. For example, OD1 may be about 0.014 inches or less. It is worthy of note that shaft 12 may include a region that tapers distally. The tapered region would, thus, have a decreased outside diameter. Generally, OD1 is the outside diameter of shaft 12 at locations proximal to the tapered region.

When using a typical guidewire/filter combinations, the potential exists that a catheter may be advanced over or past the filter. If this occurs, the interventional device may engage the proximal end of the filter and close it inadvertently and/or cause jamming of the devices together. Stop 16 has an outside diameter OD2 that is generally larger than OD1. In particular, OD2 of stop 16 is designed to be large enough to substantially prevent medical devices passing over shaft 12 from passing over and/or damaging filter 16. For example, OD2 may be about 0.026 inches or less.

In general, a size relationship exists between OD1, OD2, and the inside diameter of a medical device to passed over shaft 12. Thus, the inside diameter of the medical device is sized to be larger than OD1 so that the medical device can be advanced over shaft 12. Additionally, OD2 is sized to be larger than the inside diameter of the medical device so that the medical device cannot pass stop 16. The relative sizes are configured so that OD2 is the largest (e.g., about 0.022 to 0.030 inches), the inside diameter of the medical device is next largest (e.g., about 0.013 to 0.022 inches), and OD1 is the smallest (e.g., about 0.010 to 0.016 inches). It can be appreciated that the actual sizes of these elements are not intended to limit the invention and can be varied without altering the contemplated scope of the invention.

As stated above, stop 16 is coupled to shaft 12. Being coupled to shaft 12 is understood to include being directly attached to shaft 12, being attached to another device disposed adjacent shaft 12 (e.g., tube 18 as described below), or any other suitable attachment. Stop 16 may be coupled to shaft 12 by any suitable technique. For example, stop 16 may be coupled to shaft 12 by adhesive bonding, thermal bonding, soldering, etc. Stop 16 may be comprised of any suitable material. In some embodiments, stop 16 is comprised of a polymer, metal, or metal-polymer composite. Alternatively, stop 16 may be comprised of or be plated with a radiopaque material. Radiopaque materials are understood to generally produce a relatively bright image on a fluoroscopy screen during a medical procedure. This relatively bright image aids the user of device 10 in determining its location. Radiopaque materials include, but are not limited to, gold, platinum, and plastic material loaded with a radiopaque filler.

In some embodiments, filter 14 is coupled to a tube 18 slidably disposed over shaft 12. Tube 18 is adapted and configured to allow filter 14 to be advanced over shaft 12 to a desired location. Tube 18 may be held in position by a first stop 20 (e.g., located near the distal end 22 of shaft 12), and a second stop 24 (e.g., generally located proximally of first stop 20). In some embodiments, stop 16 may be attached to tube 18.

Stop 16 and/or filter 14 may be adapted and configured to delivery a pharmacological agent. For example, stop 16 may be coated with pharmacological agent such that stop 16 will elute or release the agent. Alternatively, the agent could be releasably encapsulated within stop 16 so that the agent can be released over a period of time within the bloodstream. In another alternative, shaft 12 or another elongate shaft or other suitable element may physically alter stop 16 (e.g., by stimulation with force, electrical current, heat, etc.) so as to cause the agent to be released. Moreover, the physical means for releasing the agent may be controllable by the clinician so that the clinician can release the agent at any desired point in time.

A number of different pharmacological agents may be used in conjunction with stop 16. The therapeutic agent may be generally described as a drug, chemotherapeutic, antibiotic, etc. Additionally, the pharmacological agent may include anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants such as D-Phe-Pro-Arg chloromethyl keton, an RGD peptide-containing compound, heparin, antithrombin compounds, platelet receptor antagonists, anti-thrombin anticodies, anti-platelet receptor antibodies, aspirin, prostaglandin inhibitors, platelet inhibitors and tick antiplatelet peptides; vascular cell growth promotors such as growth factor inhibitors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; and cholesterol-lowering agents; vasodilating agents; agents which interfere with endogenous vascoactive mechanisms; anti-sense DNA and RNA; and DNA coding for (and the corresponding proteins) anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin like growth factor, cell cycle inhibitors including CD inhibitors, thymidine kinase ("TK") and other agents useful for interfering with cell proliferation, and the family of bone morphogenic proteins ("BMP's") including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, BMP-16, "hedgehog" proteins.

Shaft 12 includes a proximal end 26 and distal end 22. Shaft 12 may comprise any elongate medical device such as a guidewire, catheter (guide, diagnostic, or therapeutic), endoscopic device, arthroscopic device, etc. Shaft 12 can be made of any material suitable including metals, metal alloys, polymers, or the like, or combinations or mixtures thereof. Some examples of suitable metals and metal alloys include stainless steel, such as 304v stainless steel, nickel-titanium alloy, such as nitinol, nickel-chromium alloy, nickel-chromium-iron alloy, cobalt alloy, or the like, or other suitable material. The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL).

The entire shaft 12 can be made of the same material, or in some embodiments, can include portions or sections made of different materials. In some embodiments, the material used to construct shaft 12 is chosen to impart varying flexibility and stiffness characteristics to different portions of shaft 12. For example, the material composition adjacent proximal end 26 of shaft 12 may be relatively stiff for pushability and torqueability, and the material composition adjacent distal end 22 of shaft 12 may be relatively flexible by comparison for better lateral trackability and steerability. Relatively stiff materials, for example, may include straightened 304v stainless steel wire, and relatively flexible materials may include, for example, a straightened super elastic or linear elastic alloy (e.g., nickel-titanium) wire. In addition, shaft 12 may generally taper near distal end 22.

Shaft 12 may also include a distal tip 28. Distal tip 28 may comprise a "spring tip" or "floppy tip" similar to analogous tips known in the art. For example, distal tip 28 may comprise a coil or spring that helps make distal end 22 generally atraumatic to blood vessel walls, body organs, and tissue when advancing device 10 through the vasculature.

Filter 14 and/or tube 18 may be disposed near distal end 22 of shaft 12. Filter 14 may generally comprise a number of configurations known to those skilled in the appropriate art. Filter 14 may include a filter frame 30, a filter material 32 disposed over frame 30, and one or more struts 34. In general, filter 14 operates between a first generally collapsed configuration and a second generally expanded configuration for collecting debris in a body lumen. Frame 30 may be comprised of a "self-expanding" shape-memory material such as nickel-titanium alloy (to bias filter 14 to be in the second expanded configuration). Filter material 32 may be comprised of a polyurethane sheet and include at least one opening that may be, for example, formed by known laser techniques. The holes or openings are sized to allow blood flow therethrough but restrict flow of debris or emboli floating in the body lumen or cavity.

Strut 34 may be coupled to tube 18 (or shaft 12) by a coupling 36. Coupling 36 may be one or more windings of strut 34 about tube 18 (or shaft 12) or be a fitting disposed over an end of strut 34 to attach it to tube 18.

The position of stop 16 can be described as being generally adjacent filter 16. In some embodiments, stop 16 is disposed proximally of a nose cone 38 coupled to tube 18. Stop 16 is generally located proximally of filter 14 but, as described above, could also be described as being attached to shaft 12, attached to tube 18, etc.

Figure 2:
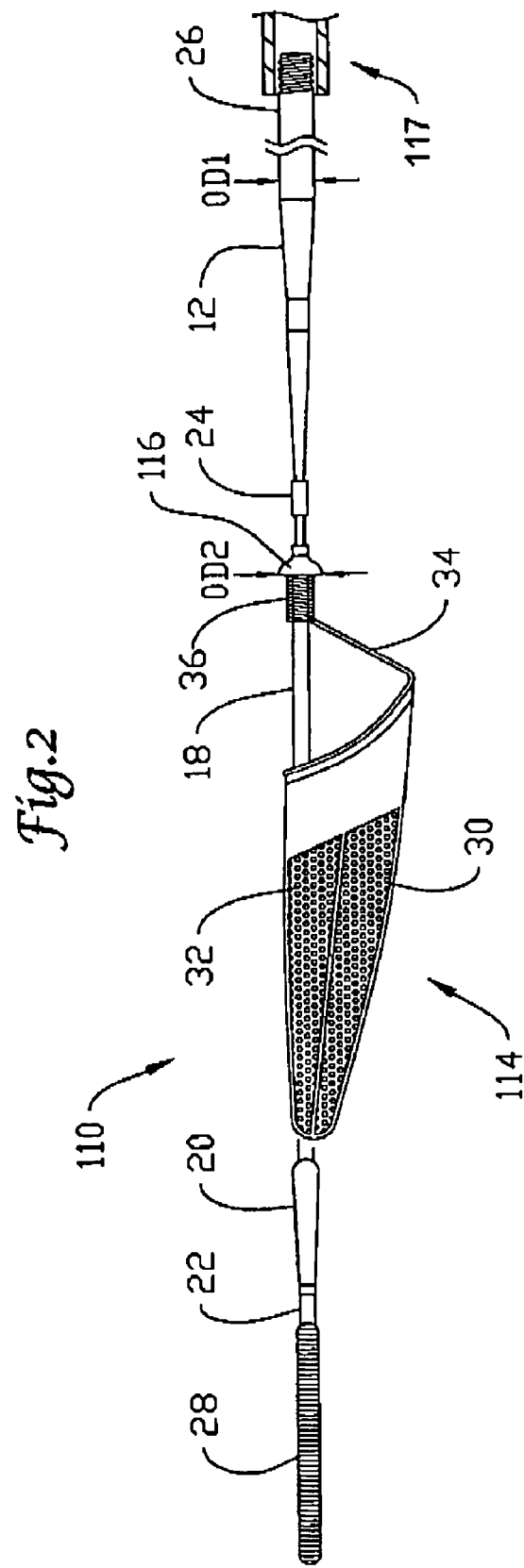
FIG. 2 is a side view of another embodiment of an embolic protection filtering device.

FIG. 2 is a side view of another example embolic protection filtering device 110 that is essentially the same in form and function as device 10 except that the position of stop 16 is altered. It can be seen in FIG. 2 that stop 116 is positioned just proximal of coupling 36. This position may allow, for example, filter 114 to collapse to a lower profile. It can be appreciated that the precise location of stop 116 may be altered to essentially any location proximal of the distal end of filter 114 without departing from the spirit of the invention. For example, stop 116 may be attached to shaft 12, attached to tube 18, etc. Stop 116 has an OD2 similar to stop 16 and is designed to be large enough to substantially prevent medical devices passing over shaft 12 from engaging the proximal end of the filter and close it inadvertently and/or cause jamming of the devices together.

From FIG. 2 it can also be seen that the dimensions of device 110 (or device 10) and components thereof may be altered. For example, filter 114 has a shape that is more elongated than filter 14. In general, the length of filter 14/114 (measured from the distal end to strut 34) may range from about 10 to 30 millimeters. Additionally, the length of distal tip 28 may be varied (e.g., between about 15-40 millimeters), the spacing between filter 14/114 and stop 16/116 may be varied (e.g., between about 5 to 15 millimeters), the spacing between distal tip 28 and first stop 20 may be varied (e.g., between about 0 to 5 millimeters), and the spacing between the distal end of tip 28 and the proximal end (e.g., at the junction of filter 14/114 or at the junction of frame 30 and strut 34) of filter 14/114 may be varied (e.g., between about 45 and 60 millimeters). The shapes, lengths, and dimensions listed above are provided as examples, and should not be interpreted to limit the claimed invention.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. An embolic protection filtering device, comprising:
   an elongate shaft having a proximal end, a distal end and a distal portion, the elongate shaft extending through at least a portion of a catheter lumen;
   a first stop coupled to the distal portion of the elongate shaft;
   a second stop coupled to the distal portion of the elongate shaft distal of the first stop;
   a tube slidably disposed over the distal portion of the elongate shaft intermediate the proximal stop and the distal stop;
   an embolic protection filter coupled to the tube; and
   a third stop attached to the tube, wherein the third stop is configured to restrain longitudinal movement of a catheter distal of the third stop.

2. An embolic protection filtering device, comprising:
   an elongate shaft having a proximal end and a distal end;
   a catheter disposed on the elongate shaft;
   an embolic protection filter coupled to the elongate shaft at a first location and a second location; and
   a stop coupled to the elongate shaft intermediate the first location and the second location, the stop configured to restrain the catheter from advancing distally of the stop.

\* \* \* \* \*